United States Patent
Labyed (10) Patent No.: US 11,006,926 B2
(45) Date of Patent: May 18, 2021

(54) REGION OF INTEREST PLACEMENT FOR QUANTITATIVE ULTRASOUND IMAGING

(71) Applicant: Siemens Medical Solutions USA, Inc., Malvern, PA (US)

(72) Inventor: Yassin Labyed, Maple Valley, WA (US)

(73) Assignee: Siemens Medical Solutions USA, Inc., Malvern, PA (US)

( * ) Notice: Subject to any disclaimer, the term of this patent is extended or adjusted under 35 U.S.C. 154(b) by 489 days.

(21) Appl. No.: 15/907,209

(22) Filed: Feb. 27, 2018

(65) Prior Publication Data

US 2019/0261949 A1 Aug. 29, 2019

(51) Int. Cl.
*A61B 8/00* (2006.01)
*A61B 8/08* (2006.01)
*G06T 7/00* (2017.01)
*G06N 20/00* (2019.01)

(52) U.S. Cl.
CPC ............ *A61B 8/469* (2013.01); *A61B 8/5207* (2013.01); *A61B 8/5223* (2013.01); *G06N 20/00* (2019.01); *G06T 7/0012* (2013.01); *A61B 8/461* (2013.01); *G06T 2207/10132* (2013.01); *G06T 2207/20084* (2013.01); *G06T 2207/20104* (2013.01)

(58) Field of Classification Search
CPC ..... A61B 8/469; A61B 8/5207; A61B 8/5223; A61B 8/461; A61B 8/5269; A61B 8/54; A61B 8/085; G06N 20/00; G06N 20/20; G06N 20/10; G06N 7/005; G06N 5/003; G06N 3/08; G06T 7/0012; G06T 2207/10132; G06T 2207/20084; G16H 50/30
See application file for complete search history.

(56) References Cited

U.S. PATENT DOCUMENTS

| | | | |
|---|---|---|---|
| 6,193,660 B1 | 2/2001 | Jackson et al. | |
| 7,090,640 B2 | 8/2006 | Barth et al. | |
| 8,320,989 B2 | 11/2012 | Gardner et al. | |
| 9,084,576 B2 | 7/2015 | Gurcar | |
| 2009/0010511 A1 | 1/2009 | Gardner et al. | |
| 2010/0249592 A1* | 9/2010 | Langeland | G06T 7/246 600/443 |

(Continued)

FOREIGN PATENT DOCUMENTS

| | | |
|---|---|---|
| JP | 2015126955 A | 7/2015 |
| JP | 6400725 | 2/2020 |
| KR | 20170016461 A | 2/2017 |

OTHER PUBLICATIONS

Fournier, B., et al. "Quantitative ultrasound imaging at the calcaneus using an automatic region of interest," Osteoporosis Int'l 7.4 (1997) 363-369.

*Primary Examiner* — Joel Lamprecht (57) ABSTRACT

For region of interest (ROI) placement in quantitative ultrasound imaging with an ultrasound scanner, the ROI is automatically placed using anatomy detection specific to the quantification, signal processing for clutter, attenuation, or noise, and/or identification of regions of fluid. For quantification, multiple ROIs may be positioned automatically. The automatic placement may improve consistency of measures over time and between sonographers and may provide for better image quality with less influence from undesired signals. As a result, diagnosis and/or treatment may be improved.

18 Claims, 3 Drawing Sheets

(56) References Cited

U.S. PATENT DOCUMENTS

| | | |
|---|---|---|
| 2013/0066204 A1 | 3/2013 | Benson et al. |
| 2013/0345566 A1* | 12/2013 | Weitzel .................. A61B 8/488 600/445 |
| 2015/0150535 A1* | 6/2015 | Fan ..................... G01S 15/8993 600/438 |
| 2016/0287214 A1 | 10/2016 | Ralovich et al. |
| 2016/0292876 A1 | 10/2016 | Zhao et al. |
| 2017/0084023 A1 | 3/2017 | Buerger |

* cited by examiner

REGION OF INTEREST PLACEMENT FOR QUANTITATIVE ULTRASOUND IMAGING

BACKGROUND

The present invention relates to quantitative ultrasound imaging. In quantitative ultrasound imaging, the detected information is further processed to quantify a characteristic of the tissue being imaged. Rather than merely providing a B-mode image of the tissue, a characteristic of that tissue is imaged. For example, shear wave speed in the tissue is calculated using ultrasound imaging. Other examples include strain, attenuation, or backscatter measures.

For quantitative ultrasound imaging, a user typically positions a region of interest (ROI) in a B-mode image. The ROI defines the region for which the quantification is performed. To avoid delays or processing complications for quantification over the entire field of view (FOV) of the B-mode image, the user-positioned ROI defines the region of tissue for quantification. This manual ROI positioning hinders workflow and increases scan times. Moreover, operator dependency and suboptimal ROI positioning may lead to low image quality and to irreproducible results. Many users do not position the ROI in the correct location, especially where the location may be specific to the type of quantification and application. Errors in sizing the ROI may also result in low image quality and/or irreproducible results.

SUMMARY

By way of introduction, the preferred embodiments described below include methods and systems for ROI placement in quantitative ultrasound imaging with an ultrasound scanner. The ROI is automatically placed using anatomy detection specific to the quantification, signal processing for clutter, attenuation, or noise, and/or identification of regions of fluid. For quantification, multiple ROIs may be positioned automatically. The automatic placement may improve consistency of measures over time and between sonographers and may provide for better image quality with less influence from undesired signals. As a result, diagnosis and/or treatment may be improved.

In a first aspect, a method is provided for ROI placement in quantitative ultrasound imaging with an ultrasound scanner. An anatomical landmark is detected from an ultrasound image. In-phase and quadrature or radio frequency ultrasound signals are signal processed. The ultrasound scanner determines a position of an ROI in a FOV of the ultrasound image. The position of the ROI is based on the anatomical landmark and results from the signal processing. Shear wave imaging is performed by the ultrasound scanner at the position of the ROI. An image is generated for the shear wave imaging.

In a second aspect, a method is provided for ROI placement in quantitative ultrasound imaging with an ultrasound scanner. The ultrasound scanner detects a location of a liver capsule in an ultrasound image and determines a position of an ROI in a FOV of the ultrasound image. The position of the ROI is determined based on the location of the liver capsule. Shear wave imaging with the ultrasound scanner is performed at the position of the ROI. An image is generated for the shear wave imaging.

In a third aspect, a system is provided for ROI placement in quantitative ultrasound imaging. Transmit and receive beamformers, connected with a transducer, are configured to scan with ultrasound in a B-mode and a quantitative mode. An image processor is configured to locate an ROI in a B-mode FOV based on data from the scan in the B-mode, to cause the transmit and receive beamformers to perform the scan in the quantitative mode for the located ROI, and to generate an image from the scan in the quantitative mode. A display is configured to display the image from the scan in the quantitative mode.

The present invention is defined by the following claims, and nothing in this section should be taken as limitations on those claims. Further aspects and advantages of the invention are disclosed below in conjunction with the preferred embodiments and may be later claimed independently or in combination.

BRIEF DESCRIPTION OF THE DRAWINGS

The components and the figures are not necessarily to scale, emphasis instead being placed upon illustrating the principles of the invention. Moreover, in the figures, like reference numerals designate corresponding parts throughout the different views.

DETAILED DESCRIPTION OF THE DRAWINGS AND PRESENTLY PREFERRED EMBODIMENTS

Automatic ROI placement is provided in shear wave or other quantitative imaging. Signal processing, image processing, and/or application of a machine learnt network automatically position, size, and/or shape a ROI, such as for shear wave speed imaging or other acoustic radiation force impulse-based ultrasound imaging. For example, in shear wave imaging, the ROI is positioned for obtaining a single shear wave speed measurement based on an ROI or for real-time shear wave speed spatial imaging for a two or three-dimensional region.

Figure 1:
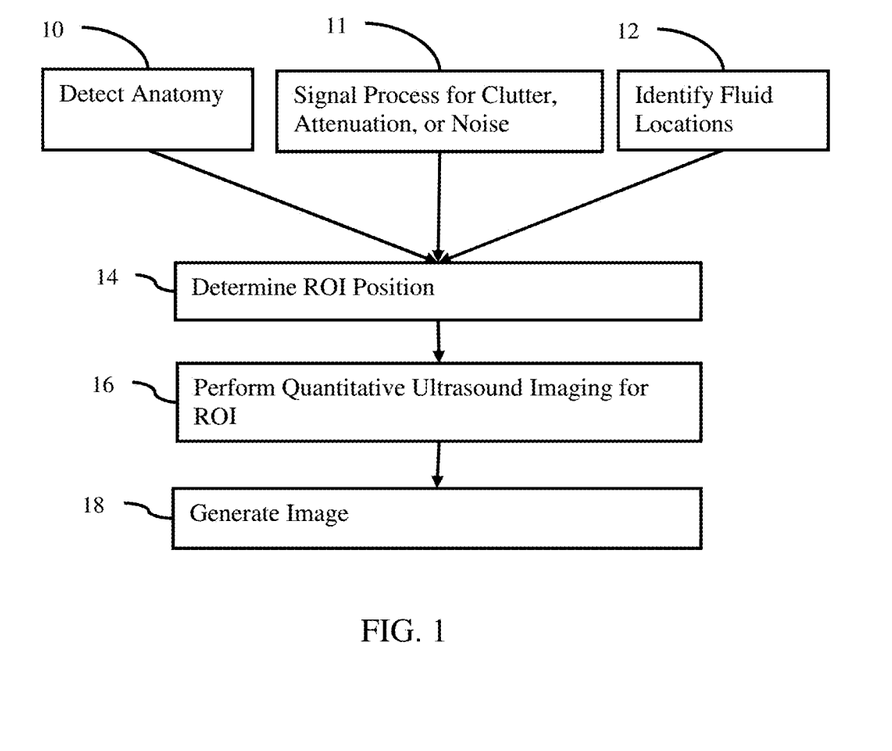
FIG. 1 is a flow chart diagram of one embodiment of a method for ROI placement in quantitative ultrasound imaging with an ultrasound scanner.

FIG. 1 shows one embodiment of a method for ROI placement in quantitative ultrasound imaging with an ultrasound scanner. In general, an object of interest spaced from the ROI location, signal processing of in-phase and quadrature (I/Q) or radio frequency (RF) data, and/or locations to be avoided (e.g., fluid locations) are used to automatically place an ROI for quantitative ultrasound imaging.

Figure 3:
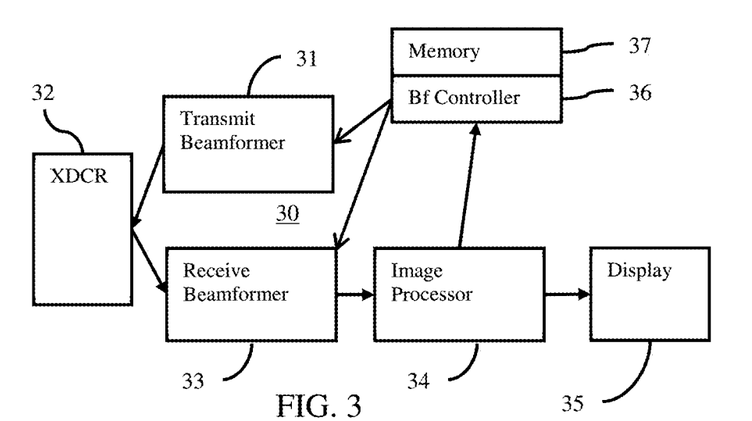
FIG. 3 is a block diagram of one embodiment of a system for ROI placement in quantitative ultrasound imaging with an ultrasound scanner.

The method is performed by the system shown in FIG. 3 or a different system. For example, a medical diagnostic ultrasound imaging system detects, signal processes, and/or identifies in acts 10, 11, and 12, an image processor determines in act 14, and the imaging system performs quantitative mode imaging and generates an image in acts 16 and 18. Other devices may perform any of the acts, such as the image processor performing all the non-scan acts.

The acts are performed in the order shown or another order. For example, acts 10, 11, and 12 are performed in any order or simultaneously.

Additional, different or fewer acts may be used. For example, one or two of acts 10, 11, and 12 are not performed. As another example, act 18 is not performed where the output is a quantification to be stored in a patient record or in a report.

To locate the ROI for quantitative imaging, ultrasound data representing or responsive to a patient is acquired. An ultrasound imaging system or scanner scans the patient. Alternatively, the data is acquired from a previous scan by the scanner, such as by transfer from a memory or picture archiving and communications system.

This scan is an initial scan, such as a first scan, or a later scan once quantitative imaging is to be used. For example, the scanning is repeated as a sonographer positions the transducer to scan the desired region of the patient. The FOV for the scanning is positioned over the organ or organs of interest. Once the object of interest is in the FOV, the ultrasound data to be used for locating the ROI is available from the scanning or is acquired by further scanning.

The scan for ultrasound data to locate the ROI is of the entire FOV. The lateral or azimuth extent and depth of the scanning define the FOV. Based on different settings, different sizes of FOV may be provided. The user or the system determines the FOV.

To scan a FOV with ultrasound, transmit and receive beams are formed by an ultrasound system. Any scan format, such as sector, linear, or Vector®, and corresponding FOV may be used. Scan lines are distributed by electric and/or mechanical steering in one, two, or three dimensions, providing data representing a line, area, or volume.

The transmit and/or receive beam characteristics may be set or responsive to values of parameters. The depth and/or lateral extent of the FOV is set. Similarly, the transmit beam focal depth, transmit frequency, receive frequency, line density, sampling density (sampling spacing along a scan line), transmit waveform (e.g., number of cycles and/or envelope shape), frame rate, aperture, and/or other scanning characteristics are set. The number of transmit focal positions per scan line (e.g., one or two) may be set. Different, additional, or fewer scan (e.g., transmit and/or receive) parameters may be used.

Through receive beamformation, the responsive data represents samples in the FOV. Data received from the scanning is detected. A B-mode detector determines the intensity of acoustic echoes represented by the received data. For example, the receive signals before detection are formatted as in-phase and quadrature (I/Q) data, but RF data may be used. A square root of a sum of the squares of the in-phase and quadrature terms is calculated as the intensity for detection. Other measures of the magnitude of the acoustic echo may be used for B-mode detection.

Other B-mode processing may be performed. For example, the detected B-mode data is spatially filtered. As another example, a sequence of frames from a corresponding sequence of scans of the entire FOV is acquired. Different pairs or other sized groupings of the resulting B-mode frames of data are temporally filtered.

In other embodiments, other types of detection and corresponding scans are performed. For example, color flow (e.g., Doppler) estimation is used. Velocity, power, and/or variance are estimated. As another example, harmonic mode is used, such as imaging at a second harmonic of a fundamental transmit frequency. Combinations of modes may be used.

Figure 2:
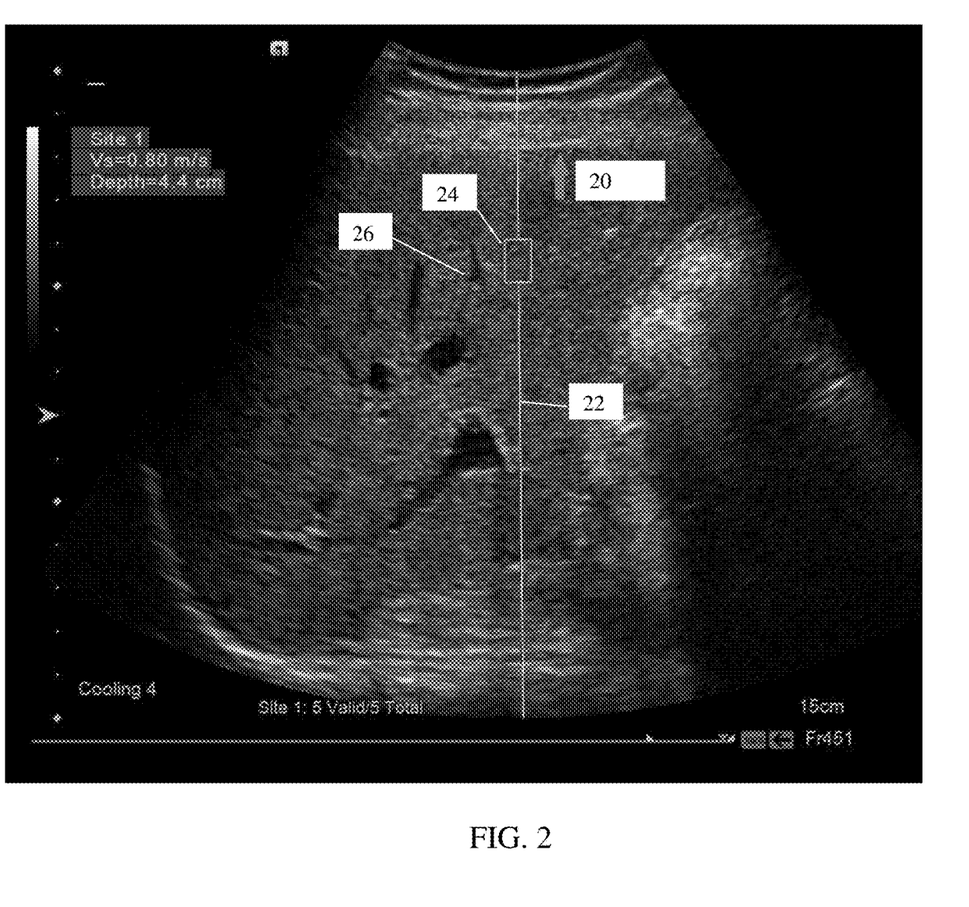
FIG. 2 is an example B-mode image with an ROI positioned for shear wave imaging of a liver.

After processing, the detected data is scan converted, if needed. A two-dimensional image may be generated. A B-mode image represents the intensity or strength of return of acoustic echoes in the B-mode FOV. FIG. 2 shows an example B-mode image for a liver of a patient. The intensities or B-mode data are mapped to gray scale within the dynamic range of the display. The gray scale may be equal or similar red, green, blue (RGB) values used by the display to control pixels. Any color or gray scale mapping may be used.

Data used for other acts is from any point in the processing path. In one embodiment, detected and scan converted scalar values are used prior to any color or display mapping. In other embodiments, beamformed samples (e.g., I/Q or RF signals) prior to detection, detected data before scan conversion, or display values after display mapping are used. The data is in the polar coordinate system used for scanning or is interpolated to a regular grid, such as a Cartesian coordinate system.

During live or real-time imaging (scanning and outputting images at the same time or while the patient has a transducer placed against them), no special interaction is generally required or expected of the user. The user may select an application (e.g., quantitative ultrasound imaging, such as shear wave speed), position the FOV, active the quantitative imaging, and then the remaining configuration automatically occurs.

The initial scan or scans of the FOV are performed prior to separate scans of the ROI for quantitative imaging. The scanning is configured to cease scans of the FOV of the patient while scanning the ROI for quantification. Alternatively, B-mode imaging and quantitative imaging are interleaved.

In act 10, the ultrasound scanner, using an image processor, detects one or more anatomical landmarks from an ultrasound image or other ultrasound data (e.g., B-mode data). The object is detected from the data of the initial or subsequent scan. The data representing the patient is image processed to detect the object. The detection is automatic during the live imaging. Rather than requiring user input of a location or locations for the object, the processor applies filtering, edge detection, pattern matching, model matching, or other computer assisted classification to detect the object in the data. Any image processing may be used. The processor detects without user input of a location or locations.

In one embodiment, a machine-learnt network is applied by the image processor (e.g., central processing unit or graphics processing unit). Haar, gradient, directional, steerable, deep learnt features, or other features are calculated from the ultrasound data and input to the machine-learnt network. The machine-learnt network, based on learning from training data with known truth distinguishing the object from other tissue, fluid or devices, indicates whether the object is represented by the data and where.

Any machine learning may be used, such as a probabilistic boosting tree, Bayesian network, neural network, deep learning, or support vector machine. Any feature or feature set may be used. In one embodiment, probabilistic boosting trees with marginal space learning train a classifier based on Haar and steerable features. In another embodiment, a random forest regression is used to train. In yet another embodiment, deep learning is used to define the features and learn how to relate the features to object detection.

The object to be located is any object, such as anatomy or a device. For example, a valve is located. Parts of a liver or other anatomic locations or lesions may be located. In other embodiments, devices, such as surgical instruments or implants (e.g., catheter, tool shaft, needle, or surgical device such as a prosthetic annulus or valve), are detected instead of anatomy. Anatomy and added devices may both be detected. Different or the same detector detects the different anatomy and/or devices. The object is any anatomic region, catheter (e.g., lasso), or tool that machine-learnt or other detectors detect.

In a shear wave imaging example, the object is a liver capsule. The location of the liver capsule is detected in an ultrasound image. FIG. 2 shows the location (e.g., arrow pointing to the liver capsule 20) of the liver capsule 20 in a B-mode image. Other anatomical features, such as the edge of the liver capsule 20, may be detected.

The detected anatomy or device has any spatial extent. For example, the anatomy extends by multiple pixels in one or more dimensions. The anatomy has any shape, such as a smoothly varying curved shape. Jagged or flat portions may occur. A device may have a smooth surface. The detection provides a location of the object (i.e., landmark) of interest. Features, surfaces, and/or interior portions of the object may be found. Features represented by the data but not belonging to the object may be used to locate the object.

In act 11, the ultrasound scanner, using the receive beamformer, beamformer controller, or image processor, signal processes ultrasound signals. The I/Q or RF data generated by the receive beamformer prior to B-mode detection, Doppler estimation, or other detection is processed.

The signal processing allows detection of characteristics reflected in relative phasing or other signal content between locations. For example, the amount of clutter, attenuation, backscatter, and/or noise is found for different locations. In one embodiment, the clutter level is measured from the ultrasound signals. The I/Q or RF data from different scan lines are correlated. The level of correlation (i.e., correlation coefficient) indicates the amount of clutter. Data that is not well correlated for adjacent scan lines may be subject to clutter. The clutter may interfere with quantification. Any now known or later developed clutter measurement may be used.

In another embodiment, the attenuation is measured. The rate of decay as a function of depth after accounting for depth gain and/or system effects is measured for different locations. The decrease in magnitude of the signals over depth or away from the transducer may be different for different tissues and/or scan settings. The rate of decay of the signal over depth (i.e., attenuation) depths corresponds with less signal or signal-to-noise ratio. Quantification may be less accurate where the attenuation is greater. Any now known or later developed attenuation measurement may be used.

In act 12, the ultrasound scanner identifies one or more locations of fluid. Doppler scanning is performed. Due to filtering, the Doppler estimates of velocity, energy, and/or variance indicate fluid response to the ultrasound. Alternatively, image processing of act 10 is performed to identify tissue structure surrounding fluid or fluid, which may appear as dark or weak return in B-mode.

Clustering, image processing (e.g., edge detection or thresholding), machine-learnt classifier, or other technique is applied to the Doppler estimates to identify regions of fluid. Low pass filtering may be applied to remove small outliers of fluid response. A threshold for length, area, or volume may be applied to remove single or small groups of locations, leaving larger locations of fluid.

The fluid regions correspond to blood, cysts, or other fluids. FIG. 2 shows some fluid regions 26 corresponding to vessels in the liver. Cysts include enough fluid content to respond to ultrasound as fluidic. Due to the difference in response to ultrasound of fluid as compared to tissue, quantification may not operate correctly or well in fluid regions. For example, measuring shear waves in a cyst may be inaccurate.

Similarly, bone, medical devices, or other solid objects relative to soft tissue may be identified. Thresholding or other image processing of B-mode data may indicate locations of bone. After filtering or other grouping, locations of bone are identified. Bone may have a different acoustic response, so may interfere with quantification.

In act 14, the ultrasound scanner, such as using an image processor or controller, determines a position of an ROI in a FOV of the ultrasound image. In one embodiment, a machine-learnt network is applied. Any of the machine learning discussed above may be used. The machine-learnt network associates input features, such as the landmark location, clutter levels by location, and/or fluid locations to placement of the ROI. Expert placed ROIs are used as ground truth for training. The machine learns to use the designated inputs (e.g., information from acts 10, 11, and/or 12) to place the ROI based on the ground truth. In other embodiments, the B-mode image is also input or is input instead of the landmark and/or fluid locations. The machine training learns to place the ROI given the input image and locations of clutter, attenuation, or other signal processing output. The application of the machine-learnt network outputs a position for the ROI. Alternatively, multiple possible positions are output, and rules are used to select the ROI position, such as based on avoiding clutter or fluid.

In an alternative embodiment, the determination uses rules. For example, the ROI is positioned relative but spaced away from a landmark while also avoiding clutter and fluid. The rules may indicate a specific orientation and distance from the landmark with tolerances for orientation and distance to account for avoiding clutter and fluid. Fuzzy logic may be used.

The position is determined from the information gathered in one or more of acts 10, 11, and/or 12. The landmark or landmarks, attenuation, clutter, and/or fluid locations are used to position the ROI. The ROI defines a scan region for quantification. Locations outside the ROI but in the FOV are not used or are used with less density than in the ROI.

In the example of FIG. 2, shear wave speed is measured in the liver. The ROI 24 is positioned relative to the liver capsule 20. The edge of the liver capsule 20 is a landmark. A line 22 perpendicular to the edge is defined. Various lines are possible. A line through the center of the liver capsule 20 or centered in the FOV is used. The ROI 24 is to be along the line 22 at a minimum distance away from the edge of the liver capsule 20. For example, the ROI 24 is to be at least 2 cm away from the edge of the liver capsule 20. Rather than detecting an object or landmark over which the ROI 24 is to be located, the landmark is used to place the ROI 24 at a location spaced from the landmark. In alternative embodiments, the ROI 24 is positioned over or to include the object.

The ROI 24 may be positioned based on results from the signal processing and/or fluid identification. Locations of relatively higher clutter, locations of relatively higher attenuation, and/or fluid locations are used to place the ROI 24. The ROI 24 may be positioned to avoid such locations. For example, the ROI 24 has various possible locations distributed in the FOV and assigned default priorities. Using the priority list, each possible ROI location is tested until an ROI location is found that avoids the clutter and fluid. Alternatively, the ROI 24 is positioned to include one or more of such locations.

For shear wave imaging of the liver, the ROI 24 may be positioned based on the liver capsule 20 and to avoid fluid 26 and relatively higher clutter. The ROI 24 has various possible locations given the rules relating the ROI 24 to the edge of the liver capsule 20. Different lines and/or depths given the tolerances provide for the possible locations. Each location is checked to avoid fluid and relatively high clutter.

The ROI 24 is positioned at the location with lower clutter and no fluid. A priority ranking for the possible locations may be used. Alternatively, a cost function is used, such as weighting acceptable possible locations further from a center of the FOV as costlier.

In another embodiment, muscle fiber tissue is detected as the landmark. The direction of the muscle fiber is used to position the ROI 24. The ROI 24 is positioned so that the scanning for the quantitative imaging is along rather than across the muscle fibers.

Some information may be used to positively place the ROI 24 rather than to indicate avoidance. The liver capsule 20 is used to positively place in the examples above. Attenuation may indicate a depth of placement. For example, the attenuation may be relatively uniform in the tissue of interest. The level of attenuation indicates the depth. Where there is greater attenuation in the tissue, then the depth is shallower so that more signal reaches the ROI 24. Where there is lesser attenuation in the tissue, the depth may be greater to satisfy the spacing from the landmark.

The ultrasound scanner identifies the ROI as a scan region. The scan region is shaped based on the scan line distribution. For linear scans, the scan lines are parallel. The resulting scan region is a square or rectangular box. For sector or Vector scans, the scan lines diverge from a point on the transducer face or a virtual point positioned behind the transducer, respectively. The sector and Vector scan formats of scan lines scan in a fan shaped region. The Vector scan may be a fan shaped region without the origin point included, such as resembling a trapezoid (e.g., truncated triangle). Other shapes of scan regions may be used.

The ROI 24 has a default shape and orientation. In one embodiment, the ultrasound scanner determines a shape of the ROI at the determined position. Any shape may be used. The shape may be determined to avoid fluid, clutter, and/or a landmark. For example, the position places the ROI next to fluid locations. The shape of the ROI may be altered to avoid the fluid locations. Rather than a rectangle, a square or rectangle with a cut-off portion is used. Alternatively or additionally, the shape may be determined to include locations.

The orientation may also be determined to include or avoid certain locations. The orientation may be based on the limits on steering from a transducer, detected landmarks that may cause acoustic shadowing, and/or directional response of the tissue being quantified.

The ROI 24 has a default size. The region is any size, such as 5 mm in lateral and 10 mm in axial. In one embodiment, the ultrasound scanner determines a size of the ROI 24 at the position. The ROI 24 is sized to avoid fluid locations or relatively high clutter. Alternatively, the ROI 24 is sized to include locations of relatively higher backscatter (e.g., lower clutter and lower noise).

The quantification scan may be affected by the size of the ROI 24. For shear wave imaging and other quantification scanning, the quantification relies on repetitive scanning of the ROI 24. By sizing the ROI smaller, the speed of scanning may increase, making the quantification less susceptible to motion artifact. By sizing the ROI larger, a more representative sampling for quantification may be provided. The ROI is sized as appropriate for the type of quantification. Different sizes may be selected based on a priority and avoidance of locations that may contribute to inaccuracy or artifacts.

The ROI 24 defining the scan region for quantitative imaging is less than the entire FOV of the B-mode image. FIG. 2 shows a rectangular ROI 24 that is less than 10% of the area of the FOV of the B-mode image.

The ultrasound scanner may automatically determine positions, sizes, shapes, and/or orientations for one, two, or more ROIs 24. The measures from each ROI 24 may be compared to assist in diagnosis or treatment. The scan data from each may be combined to provide a quantification, such as using one ROI 24 as a base-line and quantifying based on a difference in measures between two ROIs 24.

For example, relative shear wave speed may indicate whether liver tissue is fatty. By positioning one ROI 24 in the liver and another ROI 24 in the kidney, a ratio of shear wave speed between the two ROIs 24 indicates whether the liver is fatty. The ratio is close to 1.0 for non-fatty. As another example, acoustic radiation force impulse (ARFI) imaging is used to measure tissue stiffness or elasticity. The relative stiffness or elasticity between multiple ROIs 24 may indicate regions for further study. As another example, relative strain (e.g., strain ratio) may indicate locations of diagnostic interest. In yet another example, ratios of relative maximum displacement of tissue in response to ARFI transmissions may be useful. Hepto-renal echogenicity ratio may be calculated using multiple ROIs 24.

In act 16, the ultrasound scanner performs the quantitative imaging. The ROI 24 or ROIs 24 as determined define the locations of scanning for the quantitative imaging. For example, shear wave imaging is performed by the ultrasound scanner by scanning at the position of the ROI 24. Shear wave imaging may be used to quantify diagnostically useful information, such as the shear wave speed in tissue, Young's modulus, or a viscoelastic property. Shear wave imaging is a type of ARFI imaging where ARFI is used to generate the shear wave, but other sources of stress and/or other types of ARFI (e.g., elasticity) imaging may be used. Other types of quantitative imaging, such as strain, elasticity, backscatter, or attenuation may be used.

For shear wave speed imaging, the ultrasound scanner measures shear wave velocities at different locations in tissue of a patient. The velocities are measured based on a travel distance and timing of a shear wave propagating from an origin to different locations in the ROI. Shear wave velocity imaging is performed with separate values of shear wave velocity being measured for different locations or combining to provide one velocity for the ROI.

The shear wave velocities are based on tissue displacements. The ultrasound system acquires tissue displacements over time (i.e., displacement profiles) for each location in the ROI, but tissue displacement as a function of location for each of different times may be used. An ARFI (e.g., pushing pulse or acoustic radiation impulse excitation) or other source of stress generates a shear wave in the tissue in or near the ROI. As the shear wave propagates through the tissue at the ROI, the tissue displaces. By scanning the tissue with ultrasound, the data for calculating the displacements over time is acquired. Using correlation or other similarity measure, the displacements represented by the scans acquired at different times are determined. The maximum displacement and/or phase shift between displacement profiles indicates the time of occurrence of the shear wave at the location or between locations. The timing and distance from origin of the shear wave are used to solve for shear wave velocity at that location. Any now known or later developed shear wave imaging may be used.

For ARFI, a beamformer generates electrical signals for focused ultrasound transmission and a transducer converts the electrical signals to acoustic signals for transmitting the pushing pulse from the transducer. An acoustic excitation is transmitted into a patient. The acoustic excitation acts as an impulse excitation for causing displacement. For example, a 400 cycle transmit waveform with power or peak amplitude levels similar or lower than B-mode transmissions for imaging tissue is transmitted as an acoustic beam. Any ARFI or shear wave imaging sequence may be used. Other sources of stress may be used, such as a thumper (mechanical impact or vibration source). The impulse excitation generates a shear wave at a spatial location.

Tissue displacements are tracked. The ultrasound system, such as an image processor of the system, tracks the displacements in response to the pushing pulse. For each of a plurality of locations, the displacement caused by the propagating shear wave is tracked. The tracking is axial (i.e., tracking displacements one-dimensionally along a scan line), but may be two or three-dimensional tracking. The tissue displacements for each location are found for any number of temporal samplings over a period during which the wave is expected to propagate by the location. By tracking at multiple locations, tissue displacement profiles of displacement over time for the different locations are provided.

To track, a transducer and a beamformer acquire echo data at different times to determine the displacement of the tissue. The displacement is detected with ultrasound scanning. For example, B-mode scans are performed to detect tissue displacement. For a given time, ultrasound is transmitted to the tissue or region of interest. For example, pulses with 1-5 cycle durations are used with an intensity of less than 720 mW/cm$^2$. Pulses with other intensities may be used. The scanning is performed for any number of scan lines. For example, eight or sixteen receive beams distributed in two-dimensions are formed in response to each transmission. After or while applying stress, B-mode transmissions are performed repetitively along a single transmit scan line and receptions along adjacent receive scan lines.

The B-mode intensity may vary due to displacement of the tissue over time. For the monitored scan lines, a sequence of data is provided representing a time profile of tissue motion resulting from the stress. By performing the transmitting and receiving multiple times, data representing the region at different times is received. By repetitively scanning with ultrasound, the position of tissue at different times is determined.

The displacement is detected for each of multiple spatial locations. For example, the velocity, variance, shift in intensity pattern (e.g., speckle tracking), or other information is detected from the received data as the displacement between two times. An ongoing or sequence of displacements may be detected for each of the locations.

In one embodiment using B-mode data, the data from different scans is axially correlated as a function of time. For each depth or spatial sampling position, a correlation over a plurality of depths or spatial sampling positions (e.g., kernel of 64 depths with the center depth being the point for which the profile is calculated) is performed. For example, a current set of data is correlated multiple times with a reference set of data. The location of a sub-set of data centered at a given location in the reference set is identified in the current set. Different relative translations between the two data sets are performed.

The level of similarity or correlation of the data at each of different offset positions is calculated. The translation with a greatest correlation represents the displacement or offset for the time associated with the current data being compared to the reference.

The displacements over time and/or space are used for calculation. In one embodiment, the displacements for different depths are combined, leaving displacements spaced in azimuth. For example, the displacements for a given scan line or lateral location are averaged over depth. As an alternative to averaging, a maximum or other selection criterion is used to determine the displacement for a given lateral location. Displacements for only one depth may be used. Displacements for different depths may be used independently.

A separate shear wave speed may be estimated for each location, such as a function of lateral distance from an origin of the shear wave. The shear wave speed is based on the displacements as a function of time and/or location. The value of the shear wave speed for each location is estimated from the displacement profile or profiles. To estimate the value in one embodiment, the peak or maximum amplitude in the displacement profile is determined. Based on a distance of the location (i.e., sub region center, end point or start point) from the source of the stress (e.g., ARFI focal position or shear wave origin), a difference in time between application of the stress and the peak amplitude indicates a velocity. In an alternative approach, the displacement profiles from different locations are correlated to find a delay or phase difference between the locations. This phase shift may be used to calculate the velocity between the locations associated with the correlated profiles. In other embodiments, analytic data is calculated from the displacement profile and phase shift is used to determine the elasticity. A difference in phase over time of the displacements of different sub regions or a zero crossing of the phase for a given sub region indicates a velocity. In yet another embodiment, the displacement as a function of location for a given time indicates a location of maximum displacement. The distance from the shear wave origin to that location and the time provide the velocity. This is repeated for other times to find the maximum velocity at each location.

The ultrasound scanner may automatically trigger the scanning for the quantitative imaging. To avoid motion artifact, timing relative to the breathing and/or cardiac cycle is used. A breath or ECG sensor provides cycle information. The scanner uses the cycle information to select times for scanning where the tissue is subject to less motion. Alternatively, the user has the patient hold their breath and manually triggers the quantitative scanning.

Other characteristics of the quantitative scan may be controlled based on the ROI position, size, shape, and/or orientation. For example, the focal position is controlled to be at a center depth of the ROI for the pushing pulse or tracking transmissions. The deepest depth of the ROI may be used to select the push and/or tracking frequency. The F# is selected to provide uniform pushing pulse or ARFI stress in the ROI (e.g., long or short length of focus).

In act 18, the ultrasound scanner generates an image for the shear wave imaging. The generated image is displayed on a display device. The image processor, renderer, or other device generates an image from the quantitative imaging for the ROI or ROIs.

The image includes one or more quantities representing tissue characteristics. An alphanumeric or graphical representation of one or more quantities may be provided, such as a shear wave speed $V_s$ for the ROI overlaid as an annotation with a B-mode image (see FIG. 2). Alternatively or additionally, the quantities for different locations are displayed. For example, the quantities for different locations in the ROI modulate the brightness and/or color so that spatial representation of the quantity is provided in the image. The spatial representation may be overlaid or included in a B-mode or other image. The quantity or quantities may be provided without other types of imaging or may be added to or overlaid with other types of ultrasound imaging.

The ROI 24 may be shown on an image before, after, or during quantitative imaging. For example, the ROI 24 is shown as a graphic on a B-mode image for the user to verify proper placement and/or to visualize the placement.

The image may include annotations or representations of relative measurements. For example, liver fat is indicated by a ratio of elasticity between the liver and the kidney. The ROIs 24 may or may not be shown in the image.

The ultrasound imaging is used for diagnosis and/or treatment guidance. Enhanced, more consistent, and/or more accurate quantitative imaging due to proper ROI placement leads to better diagnosis and/or treatment by a physician. The physician and patient benefit from the improvement as the output of the quantification is more likely accurate.

FIG. 3 shows one embodiment of a system 30 for ROI placement in quantitative ultrasound imaging. The user configures the system 30 for quantitative imaging, such as selecting an application for shear wave speed imaging in the liver. The user may alter values of one or more presets as desired. Once scanning starts and the FOV is positioned as desired, the system 30 automatically detects the landmarks, signal processes for clutter or attenuation, and/or identifies fluid locations. The ROI for quantification is positioned, and the system 30 generates an image or images showing quantifications of the tissue at the ROI.

The system 30 is an ultrasound imager or scanner. In one embodiment, the ultrasound scanner is a medical diagnostic ultrasound imaging system. In alternative embodiments, the ultrasound imager is a personal computer, workstation, PACS station, or other arrangement at a same location or distributed over a network for real-time or post acquisition imaging.

The system 30 implements the method of FIG. 1 or other methods. The system 30 includes a transmit beamformer 31, a transducer 32, a receive beamformer 33, an image processor 34, a display 35, a beamformer controller 36, and a memory 37. Additional, different or fewer components may be provided. For example, a spatial filter, a scan converter, a mapping processor for setting dynamic range, and/or an amplifier for application of gain are provided. As another example, a user input is provided.

The transmit beamformer 31 is an ultrasound transmitter, memory, pulser, analog circuit, digital circuit, or combinations thereof. The transmit beamformer 31 is configured to generate waveforms for a plurality of channels with different or relative amplitudes, delays, and/or phasing to focus a resulting beam at one or more depths. The waveforms are generated and applied to a transducer array with any timing or pulse repetition frequency. For example, the transmit beamformer 31 generates a sequence of pulses for different laterally and/or range regions. The pulses have a center frequency.

The transmit beamformer 31 connects with the transducer 32, such as through a transmit/receive switch. Upon transmission of acoustic waves from the transducer 32 in response to the generated waves, one or more beams are formed during a given transmit event. The beams are for B-mode, quantitative mode (e.g., ARFI or shear wave imaging), or other mode of imaging. Sector, Vector®, linear, or other scan formats may be used. The same region is scanned multiple times for generating a sequence of images or for quantification. The formed beams have an aperture, origin on the transducer 32, and angle relative to the transducer 32. The beams in the FOV have a desired line density and format.

The transducer 32 is a 1-, 1.25-, 1.5-, 1.75- or 2-dimensional array of piezoelectric or capacitive membrane elements. The transducer 32 includes a plurality of elements for transducing between acoustic and electrical energies. For example, the transducer 32 is a one-dimensional PZT array with about 64-256 elements. As another example, the transducer 32 is a transesophageal echocardiography (TEE) array, a volume intracardiac echocardiography (ICE) array, or a trans-thoracic echo (TTE) array.

The transducer 32 is releasably connectable with the transmit beamformer 31 for converting electrical waveforms into acoustic waveforms, and with the receive beamformer 33 for converting acoustic echoes into electrical signals. The transducer 32 includes a plug that may be plugged into an imaging system or wirelessly communicates with the imaging system. The transducer 32 transmits the transmit beams where the waveforms have a frequency and are focused at a tissue region or location of interest in the patient. The acoustic waveforms are generated in response to applying the electrical waveforms to the transducer elements. The transducer 32 transmits acoustic energy and receives echoes. The receive signals are generated in response to ultrasound energy (echoes) impinging on the elements of the transducer 32.

The receive beamformer 33 includes a plurality of channels with amplifiers, delays, and/or phase rotators, and one or more summers. Each channel connects with one or more transducer elements. The receive beamformer 33 applies relative delays, phases, and/or apodization to form one or more receive beams in response to each transmission for detection. Dynamic focusing on receive may be provided. The receive beamformer 33 outputs data representing spatial locations using the received acoustic signals. Relative delays and/or phasing and summation of signals from different elements provide beamformation. The sampling density by the receive beamformer 33 is for a range of depths. Timing is used to select the range of depths over which the sampling occurs. The receive beams have a desired scan line density at an orientation or orientations using an aperture.

The receive beamformer 33 may include a filter, such as a filter for isolating information at a second harmonic or other frequency band relative to the transmit frequency band. Such information may more likely include desired tissue, contrast agent, and/or flow information. In another embodiment, the receive beamformer 33 includes a memory or buffer and a filter or adder. Two or more receive beams are combined to isolate information at a desired frequency band, such as a second harmonic, cubic fundamental, or another band. The fundamental frequency band may alternatively be used.

For ARFI or shear wave imaging, parallel receive beamformation is used. For tracking displacements, a transmit beam covering the ROI is transmitted. Two or more (e.g., 8, 16, 32, or 64) receive beams distributed evenly or unevenly in the ROI are formed in response to each transmit beam.

The receive beamformer 33 outputs beam summed data representing spatial locations. The beam summed data is in an I/Q or RF format. Ultrasound signals are output.

The beamformer controller 36 and/or another processor configure the beamformers 12, 16. The beamformer controller 36 is a processor, application specific integrated circuit, field programmable gate array, digital circuit, analogy circuit, memory, buffer, combinations thereof, or other device for configuring the transmit and receive beamformers 12, 16. The beamformer controller 36 may use the memory 37 to acquire and/or buffer values for different beamformer parameters. Any control structure or format may be used to establish the imaging sequence for quantitative imaging, including B-mode scanning before and/or interleaved with quantitative scanning. The beamformers 12, 16 are caused to acquire data for quantitative imaging.

The image processor 34 detects, such as detecting intensity, from the beamformed samples. Any detection may be used, such as B-mode and/or color flow detection. In one embodiment, a B-mode detector is a general processor, application specific integrated circuit, or field programmable gate array. Log compression may be provided by the B-mode detector so that the dynamic range of the B-mode data corresponds to the dynamic range of the display. The image processor 34 may or may not include a scan converter.

The image processor 34 includes a controller, general processor, application specific integrated circuit, field programmable gate array, graphics processing unit, or other processor to locate an ROI and perform quantitative ultrasound imaging based on the ROI. The image processor 34 includes or interacts with the beamformer controller 36 to scan the ROI in the quantitative scanning. The image processor 34 is configured by hardware, software, and/or firmware.

The image processor 34 may be configured to locate an ROI in a B-mode FOV based on detected data from the scan in the B-mode. The ROI is located based on one or more anatomical landmarks represented in the data from the scan in the B-mode. Other modes of scanning may be used. The detection is by application of a machine-learnt network and/or by image processing. The landmark may be used to guide placement of the ROI away from, relative to, and/or over the landmark.

The image processor 34 may be configured to identify locations of fluid or cysts. Doppler estimates generated from the beamformed data indicate locations of fluid or cysts. Alternatively, tissue edges by fluid regions are located in B-mode data to identify the fluid regions.

The image processor 34 is configured to locate the ROI in the B-mode FOV based on attenuation or clutter. I/Q or RF ultrasound signals output by the beamformer are signal processed to measure clutter and/or attenuation.

The image processor 34 uses one or more of the landmark locations, attenuation, clutter, and/or fluid region to determine the location of the ROI or ROIs. Any rule set (e.g. algorithm or machine-learnt network) may be used. The position, size, shape, and orientation of the ROI or ROIs are determined.

The image processor 34 is configured to cause the transmit and receive beamformers 31, 33 to perform the scan in the quantitative mode for the located ROI. Based on the position, size, shape, and orientation of the ROI or ROIs, the ROI or ROIs are scanned for the quantitative mode of imaging. An image is generated from the scan in the quantitative mode, such as a shear wave velocity image.

The display 20 is a CRT, LCD, monitor, plasma, projector, printer or other device for displaying an image or sequence of images. Any now known or later developed display 20 may be used. The display 20 displays a B-mode image, a quantitative mode image (e.g., annotation or color modulation on a B-mode image), or other images. The display 20 displays one or more images representing the ROI or tissue characteristic in the ROI.

The beamformer controller 36, image processor 34, and/or the ultrasound system 10 operate pursuant to instructions stored in the memory 37 or another memory. The instructions configure the system for performance of the acts of FIG. 1. The instructions configure for operation by being loaded into a controller, by causing loading of a table of values (e.g., elasticity imaging sequence), and/or by being executed. The memory 37 is a non-transitory computer readable storage media. The instructions for implementing the processes, methods and/or techniques discussed herein are provided on the computer-readable storage media or memories, such as a cache, buffer, RAM, removable media, hard drive or other computer readable storage media. Computer readable storage media include various types of volatile and nonvolatile storage media. The functions, acts, or tasks illustrated in the figures or described herein are executed in response to one or more sets of instructions stored in or on computer readable storage media. The functions, acts or tasks are independent of the particular type of instructions set, storage media, processor or processing strategy and may be performed by software, hardware, integrated circuits, firmware, micro code and the like, operating alone or in combination. Likewise, processing strategies may include multiprocessing, multitasking, parallel processing, and the like. In one embodiment, the instructions are stored on a removable media device for reading by local or remote systems. In other embodiments, the instructions are stored in a remote location for transfer through a computer network or over telephone lines. In yet other embodiments, the instructions are stored within a given computer, CPU, GPU or system.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

I claim:

1. A method for region of interest (ROI) placement in quantitative ultrasound imaging with an ultrasound scanner, the method comprising:

detecting an anatomical landmark from an ultrasound image;

signal processing (a) in-phase and quadrature or (b) radio frequency ultrasound signals, the signal processing comprising measuring attenuation or clutter from the ultrasound signals;

determining, by the ultrasound scanner, a position of an ROI in a field of view of the ultrasound image, the position of the ROI determined based on the anatomical landmark and the attenuation or the clutter from the signal processing;

performing shear wave imaging with the ultrasound scanner at the position of the ROI; and generating an image for the shear wave imaging.

2. The method of claim 1 wherein detecting comprises detecting with a machine-learnt network.

3. The method of claim 1 wherein detecting comprises detecting with image processing.

4. The method of claim 1 wherein detecting comprises detecting a liver capsule, and wherein determining comprises determining the position of the ROI based on a location of the liver capsule.

5. The method of claim 1 wherein signal processing comprises measuring the clutter from the ultrasound signals, and wherein determining comprises determining the position away from locations for the signals having the clutter.

6. The method of claim 1 wherein signal processing comprises measuring the attenuation from the ultrasound signals, and wherein determining comprises determining a depth of the position of the ROI based on the attenuation.

7. The method of claim 1 wherein determining the position comprises determining with a machine-learnt network.

8. The method of claim 1 wherein generating the image comprises generating the image with an annotation for a shear wave characteristic.

9. The method of claim 1 wherein generating the image comprises generating a shear wave image showing shear wave characteristic as a function of location in the ROI.

10. The method of claim 1 further comprising determining, by the ultrasound scanner, a size of the ROI at the position.

11. The method of claim 1 further comprising determining, by the ultrasound scanner, a shape of the ROI at the position.

12. The method of claim 1 further comprising identifying, by the ultrasound scanner, locations of fluid, and wherein determining the position comprises determining the position of the ROI to not include the locations of the fluid.

13. The method of claim 1 wherein determining the position comprises determining, by the ultrasound scanner, the position of the ROI and another position of another ROI, and wherein generating the image comprises generating the image annotated with a relative measurement between the ROI and the other ROI.

14. A method for region of interest (ROI) placement in quantitative ultrasound imaging with an ultrasound scanner, the method comprising:
  detecting, by the ultrasound scanner, a location of a liver capsule in ultrasound image;
  signal processing (a) in-phase and quadrature or (b) radio frequency ultrasound signals, the signal processing measuring clutter or attenuation;
  determining, by the ultrasound scanner, a position of an ROI in a field of view of the ultrasound image, the position of the ROI determined to be positioned away from the location of the liver capsule and determined based on the clutter or attenuation;
  performing shear wave imaging with the ultrasound scanner at the position of the ROI; and
  generating an image for the shear wave imaging.

15. The method of claim 14 wherein determining the position comprises determining the position as a minimum distance away in depth from the location of the liver capsule along a line that is perpendicular to an edge of the liver capsule.

16. A system for region of interest (ROI) placement in quantitative ultrasound imaging, the system comprising:
  transmit and receive beamformers, connected with a transducer, configured to scan with ultrasound in a B-mode and a quantitative mode;
  an image processor configured to locate an ROI in a B-mode field of view based on data from the scan in the B-mode, to cause the transmit and receive beamformers perform the scan in the quantitative mode for the located ROI, and to generate an image from the scan in the quantitative mode, wherein the image processor is configured to locate the ROI based on attenuation or clutter determined from (a) in-phase and quadrature or (b) radio frequency ultrasound signals and based on the data from the scan in the B-mode after B-mode detection;
  a display configured to display the image from the scan in the quantitative mode.

17. The system of claim 16 wherein the quantitative mode comprises acoustic radiation force imaging.

18. The system of claim 16 wherein the image processor is configured to locate the ROI based on an anatomical landmark represented in the data from the scan in the B-mode.

* * * * *